United States Patent
Kojima

(10) Patent No.: US 12,193,633 B2
(45) Date of Patent: Jan. 14, 2025

(54) MEDICAL CONTROL DEVICE AND MEDICAL OBSERVATION SYSTEM

(71) Applicant: Sony Olympus Medical Solutions Inc., Tokyo (JP)

(72) Inventor: Koji Kojima, Tokyo (JP)

(73) Assignee: Sony Olympus Medical Solutions Inc., Tokyo (JP)

(*) Notice: Subject to any disclaimer, the term of this patent is extended or adjusted under 35 U.S.C. 154(b) by 53 days.

(21) Appl. No.: 17/504,518

(22) Filed: Oct. 19, 2021

(65) Prior Publication Data
US 2022/0225857 A1    Jul. 21, 2022

(30) Foreign Application Priority Data

Jan. 18, 2021 (JP) .................................. 2021-006010

(51) Int. Cl.
| | |
|---|---|
| A61B 1/00 | (2006.01) |
| A61B 1/04 | (2006.01) |
| A61B 1/06 | (2006.01) |
| A61B 1/227 | (2006.01) |
| A61B 1/313 | (2006.01) |

(Continued)

(52) U.S. Cl.
CPC ...... *A61B 1/00006* (2013.01); *A61B 1/00009* (2013.01); *A61B 1/042* (2013.01); *A61B 1/0669* (2013.01); *A61B 1/227* (2013.01); *A61B 1/3132* (2013.01); *G06V 10/255* (2022.01); *G06V 20/00* (2022.01); *H04N 23/71* (2023.01); *H04N 23/72* (2023.01); *A61B 1/127* (2013.01); *A61B 1/128* (2013.01); *G06V 2201/034* (2022.01)

(58) Field of Classification Search
CPC . A61B 1/00006; A61B 1/00009; A61B 1/042; A61B 1/0669; A61B 1/227; A61B 1/3132; A61B 1/127; A61B 1/128; A61B 1/000095; A61B 1/0655; G06V 10/255; G06V 20/00; G06V 2201/034; G06V 2201/03; H04N 23/71; H04N 23/72
See application file for complete search history.

(56) References Cited

U.S. PATENT DOCUMENTS 4,219,014 A * 8/1980 Oshiro ................. A61B 1/0669
 396/17
5,647,840 A * 7/1997 D'Amelio .......... A61B 1/00091
 600/176

(Continued)

FOREIGN PATENT DOCUMENTS

| JP | H10192232 A | 7/1998 |
|---|---|---|
| JP | 2002112958 A | 4/2002 |

(Continued)

*Primary Examiner* — Timothy J Neal
(74) *Attorney, Agent, or Firm* — XSENSUS LLP

(57) ABSTRACT

A medical control device includes: a captured image acquisition unit configured to acquire a captured image generated by an image sensor capturing a subject image introduced by an endoscope; a luminance calculation unit configured to calculate a luminance level of the subject image included in the captured image; and a dimming controller configured to control a light amount of irradiation light onto a subject and an electronic shutter of the image sensor based on the luminance level, and execute first dimming control of narrowing the electronic shutter before reducing the light amount as the luminance level increases.

20 Claims, 7 Drawing Sheets

(51) Int. Cl.
*G06V 10/20* (2022.01)
*G06V 20/00* (2022.01)
*H04N 23/71* (2023.01)
*H04N 23/72* (2023.01)
*A61B 1/12* (2006.01)

(56) References Cited

U.S. PATENT DOCUMENTS

| | | | |
|---|---|---|---|
| 2003/0184661 A1* | 10/2003 | Yubata | H04N 23/76 348/E5.041 |
| 2005/0010081 A1* | 1/2005 | Doguchi | A61B 1/0646 348/E5.038 |
| 2005/0228231 A1* | 10/2005 | MacKinnon | G01J 3/2823 348/E5.038 |
| 2007/0112253 A1* | 5/2007 | Negishi | A61B 1/0646 600/118 |
| 2007/0123751 A1* | 5/2007 | Takahashi | A61B 5/065 600/118 |
| 2007/0132839 A1* | 6/2007 | Pang | A61B 1/00059 348/65 |
| 2007/0149857 A1* | 6/2007 | Yabe | A61B 1/00059 600/117 |
| 2009/0213244 A1* | 8/2009 | Seo | H04N 23/70 348/E5.034 |
| 2010/0238278 A1 | 9/2010 | Rovegno | |
| 2012/0226102 A1* | 9/2012 | Kagaya | G02B 23/2423 600/109 |
| 2014/0371535 A1* | 12/2014 | Seto | A61B 1/00009 600/160 |
| 2016/0235285 A1* | 8/2016 | Shirota | A61B 1/128 |
| 2019/0167080 A1* | 6/2019 | Murase | A61B 1/0655 |
| 2020/0237201 A1* | 7/2020 | Mishima | A61B 1/000095 |
| 2022/0286627 A1* | 9/2022 | Steiner | H04N 23/55 |

FOREIGN PATENT DOCUMENTS

| | | | | |
|---|---|---|---|---|
| JP | 2003305007 | A | | 10/2003 |
| JP | 2007037565 | A | | 2/2007 |
| JP | 2012-85790 | A | | 5/2012 |
| JP | 2012085790 | A | * | 5/2012 |
| JP | 2018138141 | A | | 9/2018 |
| JP | 2018166990 | A | | 11/2018 |
| WO | WO-2017158906 A1 | | | 9/2017 |
| WO | WO-2018179610 A1 | * | 10/2018 | A61B 1/00 |

* cited by examiner

FIG.3
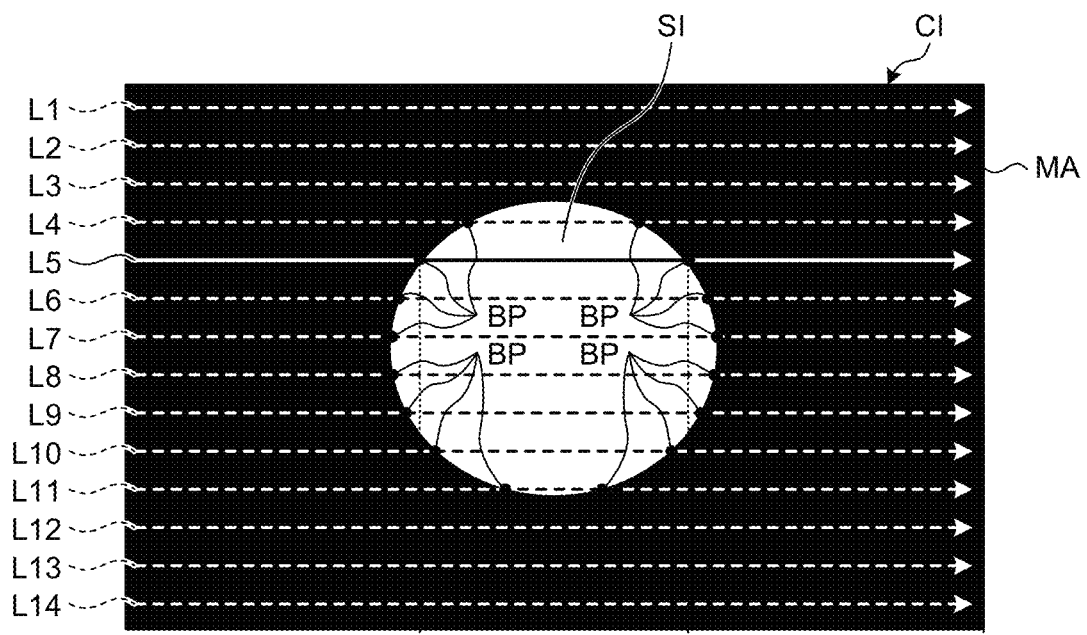
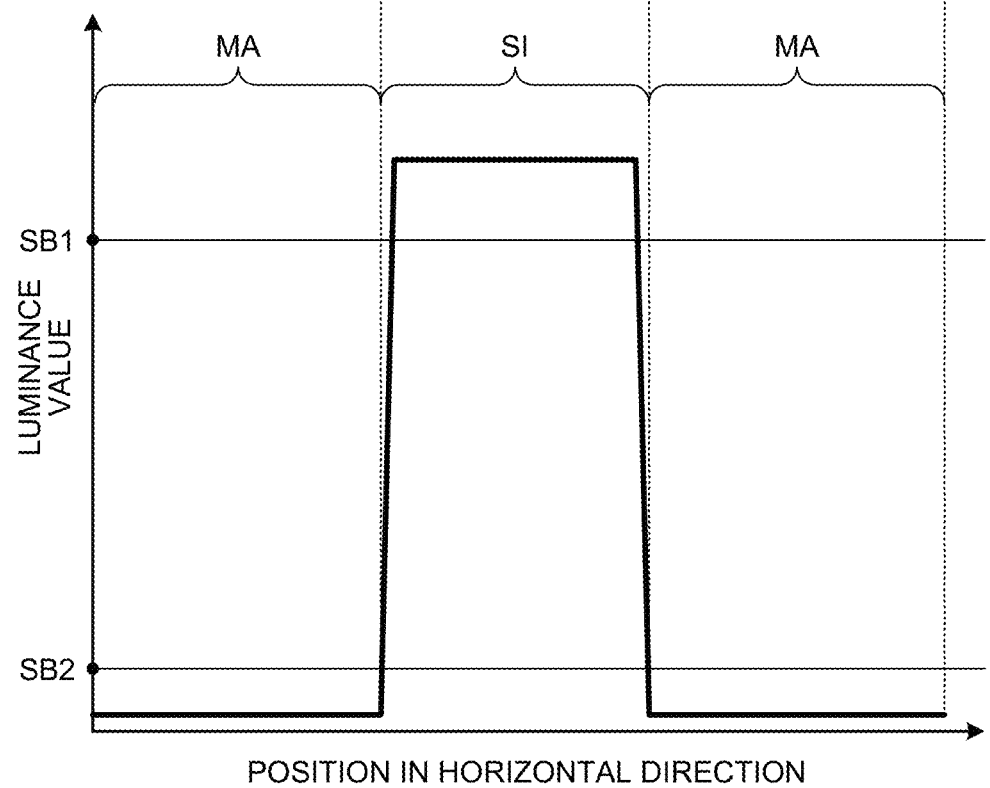

MEDICAL CONTROL DEVICE AND MEDICAL OBSERVATION SYSTEM

CROSS-REFERENCE TO RELATED APPLICATION

This application claims priority from Japanese Application No. 2021-006010, filed on Jan. 18, 2021, the contents of which are incorporated by reference herein in its entirety.

BACKGROUND

The present disclosure relates to a medical control device and a medical observation system.

In the related art, there is known a medical observation system that irradiates a subject in a living body and the like with light using a light source device, captures light (subject image) from the subject using an image sensor, and observes the subject (see, for example, JP 2012-85790 A).

In the medical observation system described in JP 2012-85790 A, dimming control for controlling the light amount of illumination light to the subject in the light source device and the electronic shutter in the image sensor is executed based on the luminance level of the subject image included in the captured image generated by the image sensor.

SUMMARY

FIG. 7 is a diagram for describing a known problem. Specifically, FIG. 7 (a) illustrates a luminance level of a subject image included in a captured image. In FIG. 7, the luminance level increases toward the right side in the drawing, and the luminance level decreases toward the left side in the drawing. FIG. 7 (b) is a diagram illustrating control of an electronic shutter in an image sensor in known dimming control. FIG. 7 (c) is a diagram illustrating control of a light amount of illumination light to a subject in a light source device in the known dimming control. Note that, in FIG. 7, a position P1 indicated by a solid line indicates a position (hereinafter, described as a dimming stable position P1) where the control of the electronic shutter and the control of the light amount are stable in a case where the subject is a specific recommended subject.

In the known dimming control, as illustrated in FIG. 7, as the luminance level of the subject image included in the captured image increases, it is common to reduce the light amount in the light source device and simultaneously narrow the electronic shutter in the image sensor.

In addition, in the known dimming control, in a case where the endoscope is an endoscope for abdominal cavities, the temperature and humidity are high in an abdominal cavity. Therefore, when the endoscope outside the abdominal cavity is inserted into the abdominal cavity, there is a problem that fogging occurs in an optical member such as a lens provided at the distal end of the endoscope and exposed to the outside of the endoscope.

According to one aspect of the present disclosure, there is provided a medical control device including: a captured image acquisition unit configured to acquire a captured image generated by an image sensor capturing a subject image introduced by an endoscope; a luminance calculation unit configured to calculate a luminance level of the subject image included in the captured image; and a dimming controller configured to control a light amount of irradiation light onto a subject and an electronic shutter of the image sensor based on the luminance level, and execute first dimming control of narrowing the electronic shutter before reducing the light amount as the luminance level increases.

BRIEF DESCRIPTION OF THE DRAWINGS

FIG. 3 is a diagram for describing a function as a type determination unit of a control unit;

DETAILED DESCRIPTION

Hereinafter, modes for carrying out the present disclosure (hereinafter, embodiments) will be described with reference to the drawings. Note that the present disclosure is not limited by the embodiments described below. Furthermore, in the description of the drawings, the same units are denoted by the same reference signs.

First Embodiment

Schematic configuration of medical observation system

Figure 1:
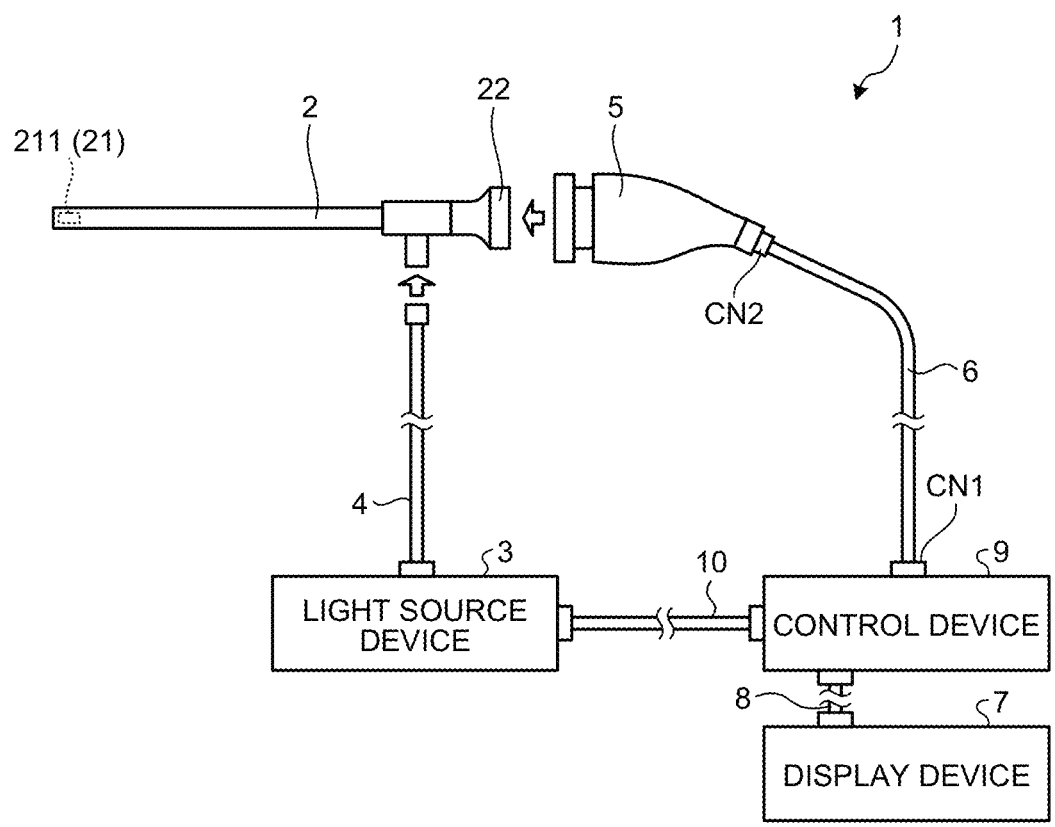
FIG. 1 is a diagram illustrating a configuration of a medical observation system according to a first embodiment.

FIG. 1 is a diagram illustrating a configuration of a medical observation system 1 according to a first embodiment.

The medical observation system 1 is a system that is used in the medical field and captures (observes) the inside of a living body as a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

The insertion unit 2 corresponds to an endoscope according to the present disclosure. In the first embodiment, the insertion unit 2 includes a rigid endoscope. That is, the insertion unit 2 has an elongated shape that is entirely rigid or partially soft and partially rigid, and is inserted into the living body. An optical system 21 (FIG. 1) that includes one or a plurality of lenses and condenses light from a subject is provided inside the insertion unit 2. Note that, in FIG. 1, for convenience of description, only an optical member 211 located at the distal end of the insertion unit 2 and exposed to the outside of the insertion unit 2 in the optical system 21 is illustrated.

In the first embodiment, the insertion unit 2 is one of two types of insertion units (endoscopes): an insertion unit (endoscope) for abdominal cavities (for laparoscopic surgery) having a large diameter; and an insertion unit (endoscope) for otology having a small diameter.

The light source device 3 is connected to one end of the light guide 4, and supplies light to irradiate the inside of the living body to the one end of the light guide 4 under the control of the control device 9.

In the first embodiment, the light source device 3 is configured separately from the control device 9, but the present disclosure is not limited to this configuration, and a configuration in which the light source device 3 is provided inside the control device 9 may be adopted.

One end of the light guide 4 is detachably connected to the light source device 3, and the other end is detachably connected to the insertion unit 2. Then, the light guide 4 transmits the light supplied from the light source device 3 from one end to the other end, and supplies the light to the insertion unit 2. The light emitted into the living body and reflected in the living body is condensed by the optical system 21 in the insertion unit 2.

The camera head 5 is detachably connected to the proximal end (eyepiece unit 22 (FIG. 1)) of the insertion unit 2. Note that the camera head 5 is detachably connected to the proximal ends of both of the above two types of insertion units 2 (for abdominal cavities and otology). Then, the camera head 5 captures the light condensed by the insertion unit 2 and generates a captured image under the control of the control device 9.

Note that a detailed configuration of the camera head 5 will be described in "Configuration of camera head" to be described later.

One end of the first transmission cable 6 is detachably connected to the control device 9 via a connector CN1 (FIG. 1), and the other end is detachably connected to the camera head 5 via a connector CN2 (FIG. 1). Then, the first transmission cable 6 transmits a captured image and the like output from the camera head 5 to the control device 9, and transmits a control signal, a synchronization signal, a clock, power, and the like output from the control device 9 to the camera head 5.

Note that, in transmission of a captured image and the like from the camera head 5 to the control device 9 via the first transmission cable 6, the captured image and the like may be transmitted as an optical signal or may be transmitted as an electric signal. The same applies to transmission of a control signal, a synchronization signal, and a clock from the control device 9 to the camera head 5 via the first transmission cable 6.

The display device 7 includes a display using liquid crystal, organic electro luminescence (EL), or the like, and displays an image based on a video signal from the control device 9 under the control of the control device 9.

One end of the second transmission cable 8 is detachably connected to the display device 7, and the other end is detachably connected to the control device 9. Then, the second transmission cable 8 transmits the video signal processed by the control device 9 to the display device 7.

The control device 9 corresponds to a medical control device according to the present disclosure. The control device 9 includes a central processing unit (CPU), a field-programmable gate array (FPGA), or the like, and integrally controls the operations of the light source device 3, the camera head 5, and the display device 7.

Note that a detailed configuration of the control device 9 will be described in "Configuration of control device" to be described later.

One end of the third transmission cable 10 is detachably connected to the light source device 3, and the other end is detachably connected to the control device 9. Then, the third transmission cable 10 transmits the control signal from the control device 9 to the light source device 3.

Configuration of Camera Head

Next, a configuration of the camera head 5 will be described.

Figure 2:
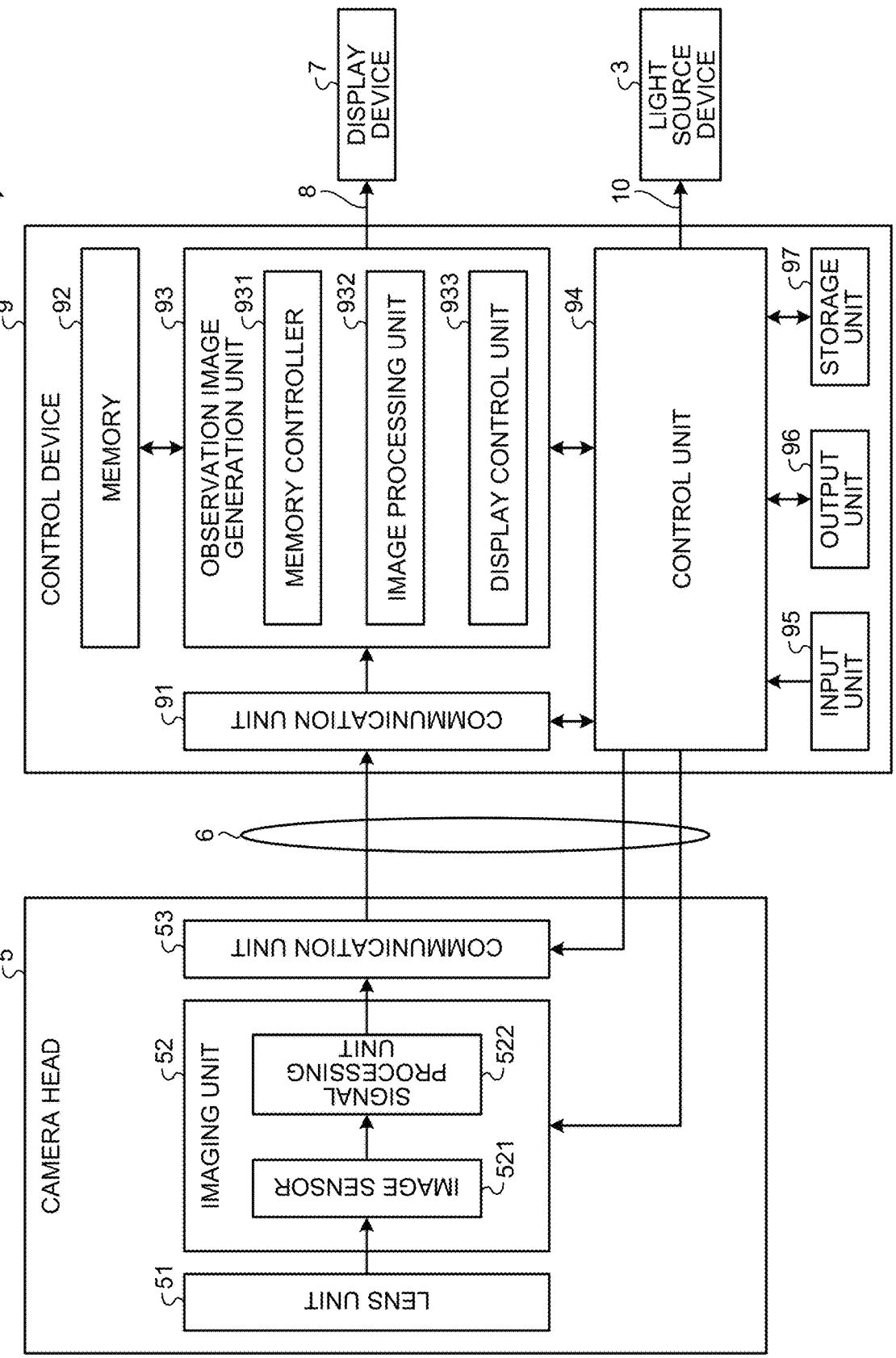
FIG. 2 is a block diagram illustrating a configuration of a camera head and a control device.

FIG. 2 is a block diagram illustrating a configuration of the camera head 5 and the control device 9.

As illustrated in FIG. 2, the camera head 5 includes a lens unit 51, an imaging unit 52, and a communication unit 53.

The lens unit 51 includes one or a plurality of lenses, and forms an image of light condensed by the insertion unit 2 on an imaging surface of the imaging unit 52 (image sensor 521). Note that, hereinafter, for convenience of description, light from the lens unit 51 toward the image sensor 521 is described as a subject image.

The imaging unit 52 captures the inside of a living body under the control of the control device 9. As illustrated in FIG. 2, the imaging unit 52 includes the image sensor 521 and a signal processing unit 522.

The image sensor 521 includes a charge coupled device (CCD), a complementary metal oxide semiconductor (CMOS), or the like that receives a subject image and converts the subject image into an electric signal (analog signal). Then, the image sensor 521 captures a subject image to generate a captured image.

Under the control of the control device 9, the signal processing unit 522 performs signal processing with respect to the captured image (analog signal) generated by the image sensor 521 and outputs the captured image (RAW signal (digital signal)).

For example, the signal processing unit 522 performs processing of removing reset noise, processing of multiplying an analog gain for amplifying the analog signal, and signal processing such as A/D conversion with respect to the captured image (analog signal) generated by the image sensor 521.

The communication unit 53 functions as a transmitter that transmits the captured image (RAW signal (digital signal)) output from the imaging unit 52 to the control device 9 via the first transmission cable 6. The communication unit 53 includes, for example, a high-speed serial interface that communicates a captured image with the control device 9 via the first transmission cable 6 at a transmission rate of 1 Gbps or above.

Configuration of Control Device

Next, a configuration of the control device 9 will be described with reference to FIG. 2.

As illustrated in FIG. 2, the control device 9 includes a communication unit 91, a memory 92, an observation image generation unit 93, a control unit 94, an input unit 95, an output unit 96, and a storage unit 97.

The communication unit 91 functions as a receiver that receives a captured image (RAW signal (digital signal)) output from the camera head 5 (communication unit 53) via the first transmission cable 6. The communication unit 91 includes, for example, a high-speed serial interface that communicates a captured image with the communication unit 53 at a transmission rate of 1 Gbps or above. That is, the communication unit 91 corresponds to a captured image acquisition unit according to the present disclosure.

The memory 92 includes, for example, a dynamic random access memory (DRAM) and the like. The memory 92 can temporarily store a plurality of frames of captured images sequentially output from the camera head 5 (communication unit 53).

The observation image generation unit 93 processes the captured images sequentially output from the camera head 5 (communication unit 53) and received by the communication unit 91 under the control of the control unit 94. As illustrated in FIG. 2, the observation image generation unit 93 includes a memory controller 931, an image processing unit 932, and a display control unit 933.

The memory controller 931 controls writing and reading of the captured image to and from the memory 92. More specifically, the memory controller 931 sequentially writes the captured images sequentially output from the camera head 5 (communication unit 53) and received by the communication unit 91 in the memory 92. In addition, the memory controller 931 reads the captured image from the memory 92 at a specific timing, and inputs the read captured image to the image processing unit 932.

The image processing unit 932 executes image processing with respect to the input captured image (RAW signal (digital signal)).

Examples of the image processing include optical black subtraction processing, white balance adjustment processing, digital gain processing (processing of multiplying a digital gain for amplifying the digital signal with respect to the digital signal), demosaic processing, color correction matrix processing, gamma correction processing, YC processing of converting an RGB signal (captured image) into a luminance color difference signal (Y, Cb/Cr signal), and the like.

The display control unit 933 generates a video signal for displaying the captured image after the image processing is executed by the image processing unit 932 under the control of the control unit 94. Then, the display control unit 933 outputs the video signal to the display device 7 via the second transmission cable 8.

The control unit 94 includes, for example, a CPU, an FPGA, or the like, and outputs a control signal via the first to third transmission cables 6, 8, and 10 to control the operations of the light source device 3, the camera head 5, and the display device 7 and to control the entire operation of the control device 9. The control unit 94 has functions as a type determination unit, a luminance calculation unit, and a dimming control unit according to the present disclosure. Note that the functions of the type determination unit, the luminance calculation unit, and the dimming control unit will be described in "Operation of control device" to be described later.

The input unit 95 includes an operation device such as a mouse, a keyboard, and a touch panel, and receives a user operation by a user such as a doctor. Then, the input unit 95 outputs an operation signal corresponding to the user operation to the control unit 94.

The output unit 96 includes a speaker, a printer, or the like, and outputs various types of information.

The storage unit 97 stores a program to be executed by the control unit 94, information necessary for processing of the control unit 94, or the like.

Operation of Control Device

Next, the operation of the control device 9 described above will be described.

Note that, for convenience of description, the function of the control unit 94 as a type determination unit, the function of the control unit 94 as a luminance calculation unit, and the function of the control unit 94 as a dimming control unit will be mainly described below.

Function as Type Determination Unit

First, the function of the control unit 94 as a type determination unit will be described.

FIG. 3 is a diagram for describing a function of the control unit 94 as a type determination unit. Specifically, FIG. 3 (a) is a diagram illustrating an example of a captured image CI captured by the image sensor 521. FIG. 3 (b) is a diagram illustrating distribution of luminance values on a horizontal line L5 in the captured image CI in FIG. 3 (a).

Here, the light (subject image) reflected in the living body and condensed inside the insertion unit 2 has a substantially circular cross section. Therefore, a subject image SI in the captured image CI has a substantially circular shape as illustrated in FIG. 3 (a). That is, the captured image CI includes a region of the subject image SI and a mask region MA (black portion in FIG. 3 (a)) other than the subject image SI.

The control unit 94 acquires a luminance signal (Y signal) out of the luminance color difference signal (Y, Cb/Cr signal) which is the captured image CI subjected to the YC processing by the image processing unit 932. Then, based on the luminance signal (Y signal), the control unit 94 detects distribution of luminance values on a plurality of (14 in the example of FIG. 3 (a)) horizontal lines L1 to L14 in the captured image CI.

Here, in the captured image CI, the region of the subject image SI has a higher luminance value than the mask region MA. That is, for example, in the luminance distribution on the horizontal line L5, as illustrated in FIG. 3 (b), the luminance value increases between the two boundary points BP of the subject image SI and the mask region MA, and the luminance value decreases in the other portions.

Therefore, the control unit 94 compares the luminance value with a first luminance threshold SB1 (FIG. 3 (b)), and recognizes a region where pixels having luminance values higher than the first luminance threshold SB1 are continuously arranged as a region of the subject image SI. In addition, the control unit 94 compares the luminance value with a second luminance threshold SB2 (FIG. 3 (b)) lower than first luminance threshold SB1, and recognizes a region where pixels having luminance values lower than second luminance threshold SB2 are continuously arranged as the mask region MA. By executing the above processing on all the horizontal lines L1 to L14, the control unit 94 recognizes the entire region of the subject image SI and the entire mask region MA in the captured image CI.

Then, the control unit 94 compares the size of the region of the subject image SI with a specific size threshold, and in a case where the size of the region of the subject image SI is equal to or larger than the size threshold, the control unit 94 determines the type of the insertion unit 2 connected to the camera head 5 to be an insertion unit (endoscope) for abdominal cavities.

On the other hand, in a case where the size of the region of the subject image SI is smaller than the size threshold, the control unit 94 determines the type of the insertion unit 2 connected to the camera head 5 to be an insertion unit (endoscope) for otology.

Function as Luminance Calculation Unit

Next, the function of the control unit 94 as a luminance calculation unit will be described.

The control unit 94 calculates a luminance level (luminance average value) in the detection region based on a luminance signal (Y signal) in the detection region that is at least a part of the entire image region of the captured image CI, of a luminance color difference signal (Y, Cb/Cr signal) that is the captured image CI subjected to the YC processing by the image processing unit 932.

Function as Dimming Control Unit

Next, the function of the control unit 94 as a dimming control unit will be described.

Based on the luminance level (luminance average value) in the detection region in the captured image CI calculated as described above, the control unit 94 executes dimming control for adjusting the captured image CI to reference brightness. Here, in a case where the type of the insertion unit 2 connected to the camera head 5 is determined to be an insertion unit for abdominal cavities, the control unit 94 executes the first dimming control as the dimming control.

That is, the first type according to the present disclosure is an insertion unit (endoscope) for abdominal cavities. On the other hand, in a case where the type of the insertion unit 2 connected to the camera head 5 is determined to be an insertion unit for otology, the control unit 94 executes the second dimming control as the dimming control. That is, the second type according to the present disclosure is an insertion unit (endoscope) for otology.

Hereinafter, the first and second dimming controls will be described in order.

First Dimming Control

First, the first dimming control will be described.

Figure 4:
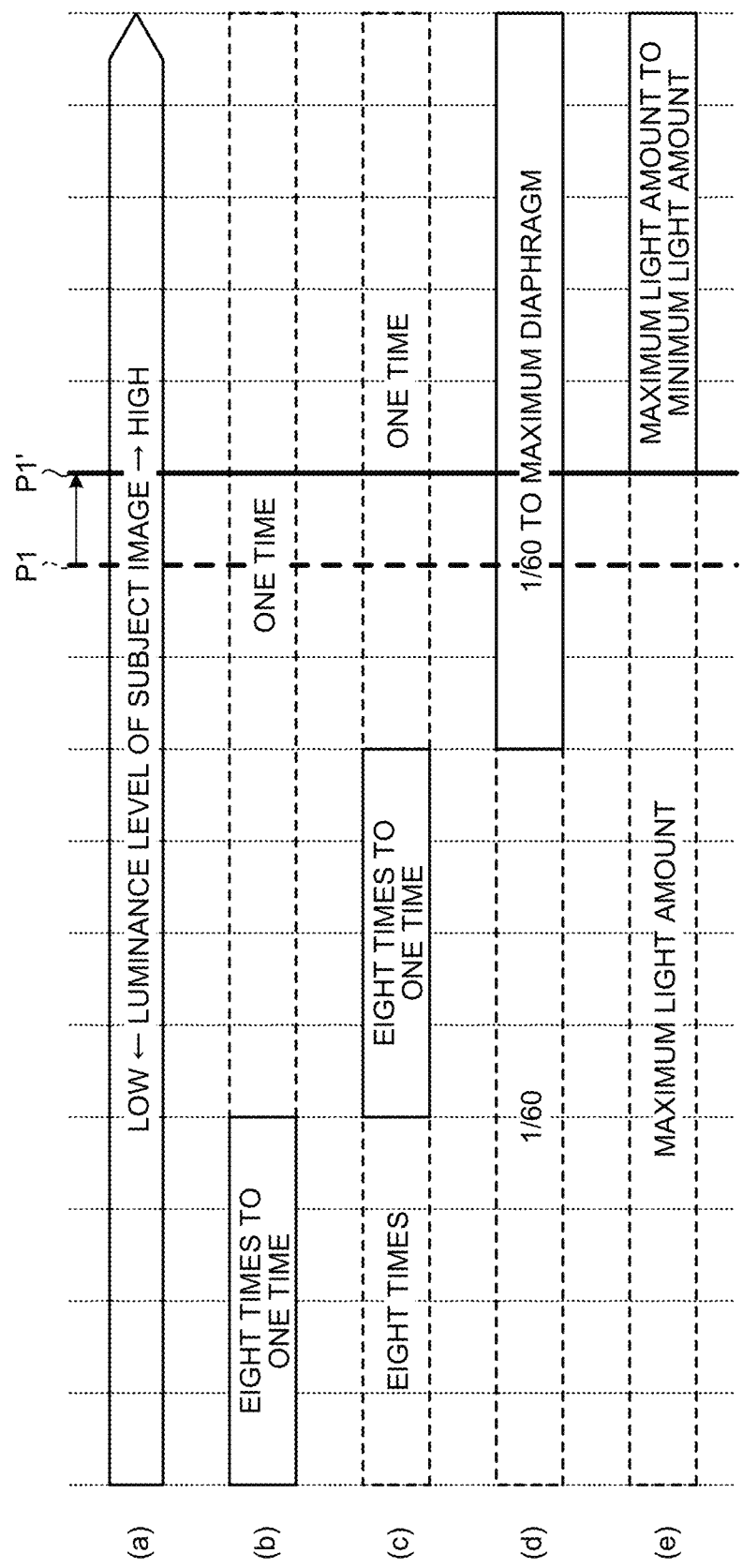
FIG. 4 is a diagram for describing first dimming control.
Figure 7:
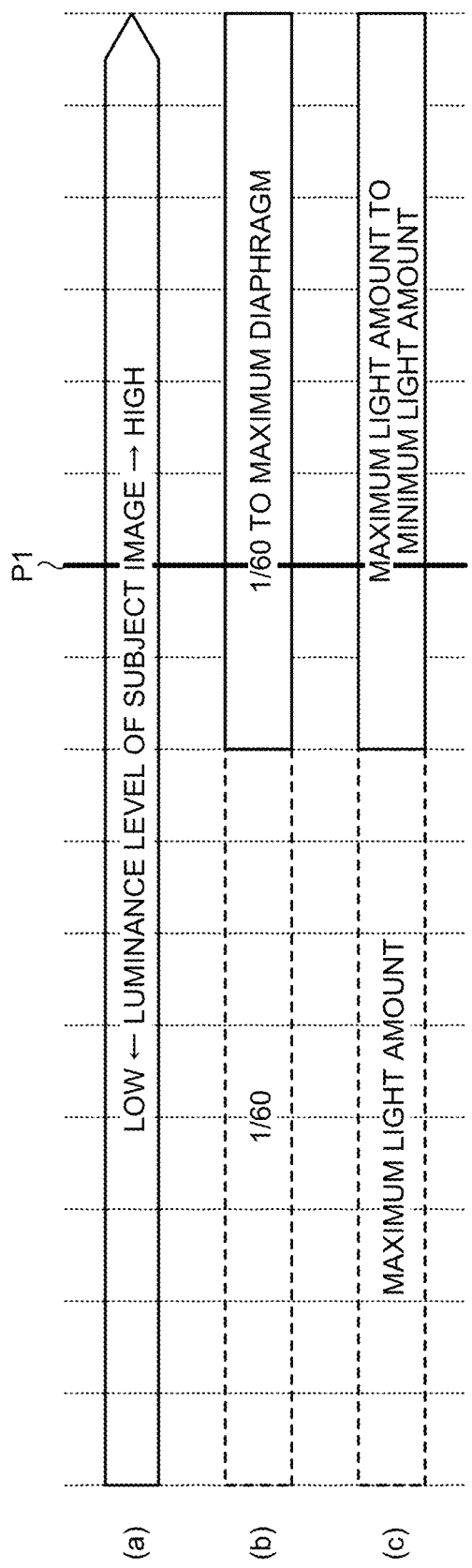
FIG. 7 is a diagram for describing a known problem.

FIG. 4 is a diagram for describing first dimming control. Specifically, FIG. 4 (a) is a diagram corresponding to FIG. 7 (a), and illustrates the luminance level in the detection region in the captured image CI calculated as described above (the luminance level of the subject image SI included in the captured image CI). In FIG. 4, as with FIG. 7, the luminance level increases toward the right in the drawing, and the luminance level decreases toward the left side in the drawing. FIG. 4 (b) is a diagram illustrating control of the digital gain multiplied in the image processing (digital gain processing) by the image processing unit 932. FIG. 4 (c) is a diagram illustrating control of the analog gain multiplied by the signal processing unit 522. FIG. 4 (d) is a diagram illustrating control of the electronic shutter in the image sensor 521. FIG. 4 (e) is a diagram illustrating control of the light amount of illumination light into the living body in the light source device 3. In FIG. 4, a position P1 indicated by a broken line indicates a dimming stable position in the known dimming control illustrated in FIG. 7. Further, in FIG. 4, a position P1' indicated by a solid line indicates a dimming stable position where the dimming control is stable by the first dimming control in a case where the subject is a specific recommended subject.

In the first dimming control, as the luminance level of the subject image SI increases, the control unit 94 first sequentially decreases the digital gain from the maximum value to the minimum value as illustrated in FIG. 4 (b). In the example of FIG. 4 (b), the maximum value of the digital gain is eight times, and the minimum value of the digital gain is one time.

In addition, in the process of decreasing the digital gain from the maximum value to the minimum value, the control unit 94 does not change the analog gain from the maximum value as illustrated in FIG. 4 (c). In the example of FIG. 4 (c), the maximum value of the analog gain is eight times. Then, as the luminance level of the subject image SI further increases, the control unit 94 sequentially decreases the analog gain from the maximum value to the minimum value at the same time as the timing when the digital gain is set to the minimum value. In the example of FIG. 4 (c), the minimum value of the analog gain is one time.

In addition, in the process of decreasing the digital gain from the maximum value to the minimum value and the process of decreasing the analog gain from the maximum value to the minimum value, the control unit 94 does not change the electronic shutter in the image sensor 521 from the minimum diaphragm as illustrated in FIG. 4 (d). In the example of FIG. 4 (d), the minimum diaphragm of the electronic shutter in the image sensor 521 is 1/60 [hour]. Then, as the luminance level of the subject image SI further increases, the control unit 94 sequentially changes the electronic shutter in the image sensor 521 from the minimum diaphragm to the maximum diaphragm at the same time as the timing when the analog gain is set to the minimum value.

In the example of FIG. 4 (d), the time of the electronic shutter is increased from 1/60 [hour].

In addition, when the electronic shutter in the image sensor 521 is kept at the minimum diaphragm, the control unit 94 does not change the light amount in the light source device 3 from the maximum light amount as illustrated in FIG. 4 (e). Note that, in the first dimming control, the maximum light amount is, for example, the light amount that can be emitted to the maximum (hereinafter, described as full light emission) in the light source device 3. Then, as the luminance level of the subject image SI further increases, the control unit 94 sequentially decreases the light amount in the light source device 3 from the maximum light amount to the minimum light amount after the timing when the electronic shutter in the image sensor 521 is changed from the minimum diaphragm to the maximum diaphragm. Note that, in the first dimming control, the minimum light amount is, for example, a light amount higher than the light amount that can be emitted at the minimum in the light source device 3. For example, as a characteristic of the light source device 3, it is possible to decrease the light amount to 1/4000 of the full light emission, but the minimum light amount is set to 1/1000 of the full light emission.

As described above, in the first dimming control, as the luminance level of the subject image SI increases, the electronic shutter in the image sensor 521 is narrowed before the light amount in the light source device 3 is reduced. In addition, in the first dimming control, as the luminance level of the subject image SI increases, both the digital gain and the analog gain are decreased before the electronic shutter in the image sensor 521 is narrowed.

Then, in the first dimming control, as illustrated in FIG. 4, the dimming stable position P1' moves to the side where the luminance level of the subject image SI is high (right side in FIG. 4) with respect to the dimming stable position P1 by the known dimming control.

Second Dimming Control

Next, the second dimming control will be described.

Figure 5:
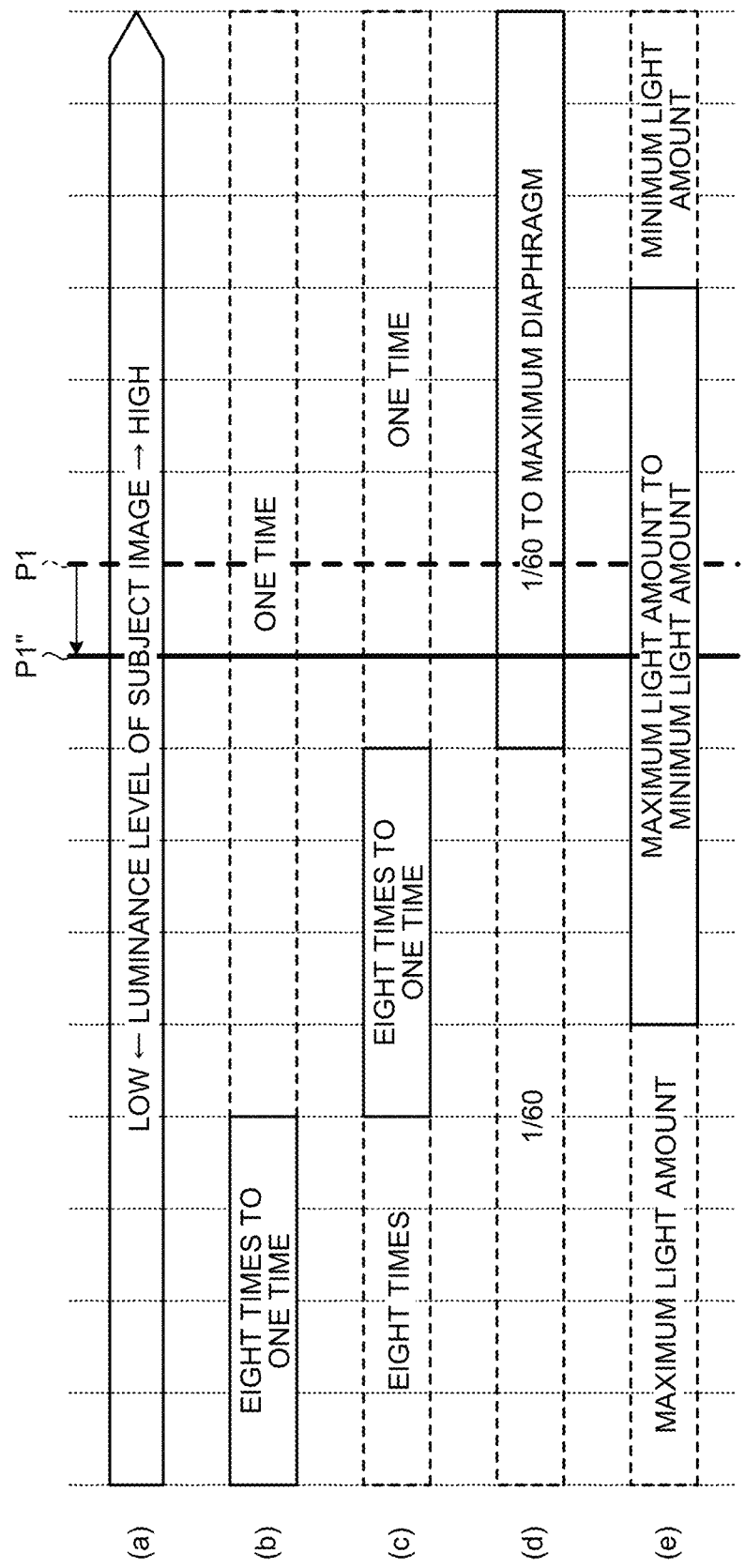
FIG. 5 is a diagram for describing second dimming control.

FIG. 5 is a diagram for describing a second dimming control. Specifically, FIGS. 5 (a) to 5 (e) are diagrams corresponding to FIGS. 4 (a) to 4 (e), respectively. In FIG. 5, a position P1 indicated by a broken line indicates a dimming stable position in the known dimming control illustrated in FIG. 7. Further, in FIG. 5, a position P1" indicated by a solid line indicates a dimming stable position where the dimming control is stable by the second dimming control in a case where the subject is a specific recommended subject.

In the second dimming control, as the luminance level of the subject image SI increases, as illustrated in FIGS. 5 (b) to 5 (d), the control unit 94 executes control of the digital gain, control of the analog gain, and control of the electronic shutter in the image sensor 521, similarly to the first dimming control.

In addition, as the luminance level of the subject image SI increases within a period in which the electronic shutter in the image sensor 521 is kept at the minimum diaphragm and is not changed (before timing at which the electronic shutter in the image sensor 521 is changed from the minimum diaphragm to the maximum diaphragm), the control unit 94 sequentially decreases the light amount in the light source device 3 from the maximum light amount to the minimum light amount as illustrated in FIG. 5 (e). In the second dimming control, the maximum light amount in the light source device 3 is, for example, 1/4 of the light amount with respect to the full light emission in the light source device 3. That is, the maximum value of the light amount in the first dimming control is larger than the maximum value of the light amount in the second dimming control. In addition, in the second dimming control, the minimum light amount in the light source device 3 is, for example, a light amount that can be emitted at the minimum in the light source device 3 (¹/4000 of the light amount with respect to full light emission). That is, the minimum value of the light amount in the first dimming control is larger than the minimum value of the light amount in the second dimming control. Then, when the light amount in the light source device 3 is decreased to the minimum light amount after the timing at which the electronic shutter in the image sensor 521 is changed from the minimum diaphragm to the maximum diaphragm, the control unit 94 does not change the light amount from the minimum light amount even if the luminance level of the subject image SI increases.

As described above, in the second dimming control, as the luminance level of the subject image SI increases, the light amount in the light source device 3 is reduced before the electronic shutter in the image sensor 521 is narrowed. In addition, in the second dimming control, as the luminance level of the subject image SI increases, both the digital gain and the analog gain are decreased before the electronic shutter in the image sensor 521 is narrowed.

Then, in the second dimming control, as illustrated in FIG. 5, a dimming stable position P1" moves to the side where the luminance level of the subject image SI is low (left side in FIG. 5) with respect to the dimming stable position P1 by the known dimming control.

According to the first embodiment described above, the following effects are obtained.

In the control device 9 according to the first embodiment, in a case where the type of the insertion unit 2 connected to the camera head 5 is an insertion unit for abdominal cavities, as the luminance level of the subject image SI included in the captured image CI increases, the first dimming control of narrowing the electronic shutter is executed before the light amount is reduced. As a result, the light amount at the dimming stable position P1' can be made higher than the light amount at the dimming stable position P1 in the known dimming control.

Therefore, it is possible to increase the temperature of the distal end of the insertion unit 2 and effectively suppress fogging caused in the optical member 211 (hereinafter, described as a first effect).

By the way, in a case where the insertion unit 2 is an insertion unit for otology, in order to avoid contact of the distal end of the insertion unit 2 having a high temperature with a portion weak to heat such as an eardrum, it is necessary to perform observation in a state in which the distal end is positioned at a position away from the observation target.

In the control device 9 according to the first embodiment, in a case where the type of the insertion unit 2 connected to the camera head 5 is an insertion unit for otology, as the luminance level of the subject image SI included in the captured image CI increases, the second dimming control of reducing the light amount is executed before the electronic shutter is narrowed. As a result, the light amount at the dimming stable position P1' can be made lower than the light amount at the dimming stable position P1 in the known dimming control.

Therefore, the temperature of the distal end of the insertion unit 2 can be decreased, and observation can be performed in a state in which the distal end is positioned at a position close to the observation target (hereinafter, described as a second effect).

In particular, the maximum value of the light amount in the first dimming control is larger than the maximum value of the light amount in the second dimming control. In addition, the minimum value of the light amount in the first dimming control is larger than the minimum value of the light amount in the second dimming control. Therefore, the first and second effects described above can be suitably realized.

In addition, the control device 9 according to the first embodiment determines the type of the insertion unit 2 based on the region of the subject image SI included in the captured image CI. Therefore, a user such as a doctor does not need to input the type of the insertion unit 2 using the input unit 95 and the like. That is, convenience can be improved.

Second Embodiment

Next, a second embodiment will be described.

In the following description, the same reference signs are given to the same configurations as those of the first embodiment described above, and a detailed description will be omitted or simplified.

Figure 6:
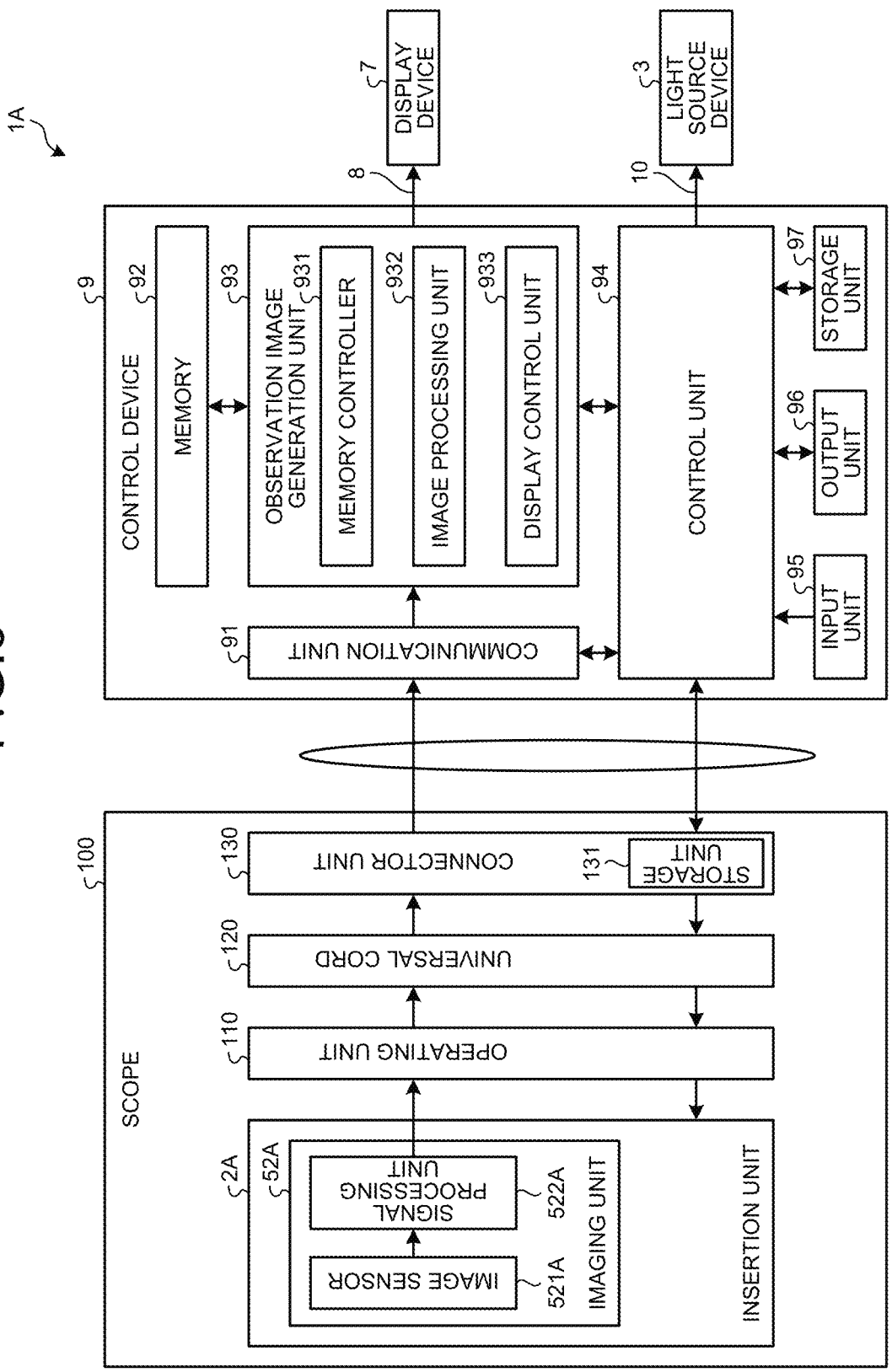
FIG. 6 is a diagram illustrating a configuration of a medical observation system according to a second embodiment.

FIG. 6 is a diagram illustrating a configuration of a medical observation system 1A according to a second embodiment.

In the medical observation system 1A according to the second embodiment, as illustrated in FIG. 6, a scope 100 is adopted instead of the insertion unit 2, the camera head 5, and the first transmission cable 6 in the medical observation system 1 described in the above first embodiment.

The scope 100 corresponds to an endoscope according to the present disclosure. Then, in the second embodiment, the scope 100 is one of two types of scopes (endoscopes): a scope (endoscope) for abdominal cavities (for laparoscopic surgery); and a scope (endoscope) for otology. Then, the scope 100 captures a subject image partially inserted into a living body and reflected in the living body, and outputs the captured image generated by the imaging. As illustrated in FIG. 6, the scope 100 includes an insertion unit 2A, an operating unit 110, a universal cord 120, and a connector unit 130.

The insertion unit 2A is a unit at least a part of which has flexibility and is inserted into a living body. A light guide (not illustrated), an illumination lens (not illustrated), an objective lens (not illustrated), and an imaging unit 52A (FIG. 6) are provided in the insertion unit 2A.

The above light guide is routed from the insertion unit 2A to the connector unit 130 through the operating unit 110 and the universal cord 120. One end of the light guide is located at the distal end in the insertion unit 2A. In addition, in a state in which the scope 100 (connector unit 130) is connected to the light source device 3, the other end of the light guide is located in the light source device 3. Note that FIG. 6 illustrates a state in which the scope 100 and the light source device 3 are separated from each other for convenience of description, but the scope 100 is also connected to the light source device 3 in addition to the control device 9. Then, the light guide transmits the light supplied from the light source device 3 from the other end to one end.

The above illumination lens faces one end of the above light guide in the insertion unit 2A. Then, the illumination lens irradiates the inside of the living body with the light transmitted by the light guide.

The above objective lens is provided at the distal end in the insertion unit 2A. Then, the objective lens forms an image of light (subject image) emitted into the living body from the above illumination lens and reflected in the living body on an image sensor 521A.

As illustrated in FIG. 6, the imaging unit 52A has a configuration similar to that of the imaging unit 52 described in the above first embodiment. That is, the imaging unit 52A includes the image sensor 521A and a signal processing unit 522A similar to the image sensor 521 and the signal processing unit 522 forming the imaging unit 52, respectively.

Here, a signal line (not illustrated) is routed from the insertion unit 2A to the connector unit 130 through the operating unit 110 and the universal cord 120. Then, one end of the signal line is connected to the imaging unit 52A (signal processing unit 522A). In addition, in a state in which the scope 100 is connected to the control device 9, the other end of the signal line is connected to the control device 9. Then, the signal line transmits a captured image (RAW signal (digital signal)) generated by the imaging unit 52A, a control signal output from the control device 9, and the like between the scope 100 and the control device 9.

The operating unit 110 is connected to the proximal end in the insertion unit 2A. Then, the operating unit 110 receives various operations with respect to the scope 100.

The universal cord 120 extends from the operating unit 110 in a direction different from the extending direction of the insertion unit 2A, and is a cord in which the above light guide, the above signal line, or the like are disposed.

The connector unit 130 is provided at the end of the universal cord 120, and is detachably connected to the control device 9 and the light source device 3. As illustrated in FIG. 6, the connector unit 130 is provided with a storage unit 131.

The storage unit 131 stores a scope ID indicating a type (scope for abdominal cavities or scope for otology) of the scope 100. The scope ID corresponds to type information according to the present disclosure.

Then, in the medical observation system 1A according to the second embodiment, the function of the control unit 94 as the type determination unit is different from that of the first embodiment described above.

That is, the control unit 94 determines the type of the scope 100 connected to the control device 9 based on the scope ID stored in the storage unit 131. Note that the function of the control unit 94 as a luminance calculation unit and the function of the control unit 94 as a dimming control unit are similar to those in the first embodiment described above.

Even in a case where the type of the scope 100 is determined based on the scope ID as in the present embodiment described above, the same effect as those of the first embodiment described above is obtained.

Other Embodiments

Although the embodiments for carrying out the present disclosure have been described so far, the present disclosure should not be limited only to the first and second embodiments described above.

In the first and second embodiments described above, both the analog gain control and the digital gain control are executed as the first and second dimming controls, but the present disclosure is not limited to this configuration, and only one of the analog gain control and the digital gain control may be executed.

In the first and second embodiments described above, the method for determining the type of the insertion unit 2 or the type of the scope 100 is not limited to the determination method described in the first and second embodiments described above. For example, the control unit 94 may be configured to determine the type when a user such as a doctor inputs the type of the insertion unit 2 or the type of the scope 100 using the input unit 95 and the like.

Note that the following configurations also belong to the technical scope of the present disclosure.

(1) A medical control device including: a captured image acquisition unit that acquires a captured image generated by an image sensor capturing a subject image introduced by an endoscope; a luminance calculation unit that calculates a luminance level of the subject image included in the captured image; and a dimming control unit that controls a light amount of irradiation light onto a subject and an electronic shutter of the image sensor based on the luminance level, in which the dimming control unit executes first dimming control of narrowing the electronic shutter before reducing the light amount as the luminance level increases.

(2) The medical control device according to (1) further including: a type determination unit that determines a type of the endoscope, in which the dimming control unit executes first dimming control in a case where the type of the endoscope is a first type, and executes second dimming control different from the first dimming control in a case where the type of the endoscope is a second type different from the first type, and the second dimming control is control in which the light amount is reduced before the electronic shutter is narrowed as the luminance level increases.

(3) The medical control device according to (2), in which the first type is an endoscope for an abdominal cavity, and the second type is an endoscope for otology.

(4) The medical control device according to (2) or (3), in which the type determination unit determines the type of the endoscope based on at least one of a region of the subject image included in the captured image and a mask region other than the subject image included in the captured image.

(5) The medical control device according to (2) or (3), in which the type determination unit determines the type of the endoscope based on type information that is stored in a storage unit provided in the endoscope and indicates the type of the endoscope.

(6) The medical control device according to any one of (2) to (5), in which a maximum value of the light amount in the first dimming control is larger than a maximum value of the light amount in the second dimming control.

(7) The medical control device according to any one of (2) to (6), in which a minimum value of the light amount in the first dimming control is larger than a minimum value of the light amount in the second dimming control.

(8) The medical control device according to any one of (1) to (7), in which the dimming control unit decreases a gain of at least one of an analog gain to be multiplied by an analog signal corresponding to the captured image and a digital gain to be multiplied by a digital signal corresponding to the captured image before narrowing the electronic shutter, as the luminance level increases.

(9) A medical control device including: a captured image acquisition unit that acquires a captured image generated by an image sensor capturing a subject image introduced by an endoscope; a luminance calculation unit that calculates a luminance level of the subject image included in the captured image; and a dimming control unit that controls a light amount of irradiation light onto a subject and an electronic shutter of the image sensor based on the luminance level, in which the dimming control unit executes second dimming control of reducing the light amount before narrowing the electronic shutter as the luminance level increases.

(10) A medical observation system including: an image sensor that captures a subject image introduced by an endoscope; a light source device that supplies irradiation light onto a subject; and a medical control device that controls operation of the image sensor and the light source device, in which the medical control device includes a captured image acquisition unit that acquires a captured image generated by the image sensor, a luminance calculation unit that calculates a luminance level of the subject image included in the captured image, and a dimming control unit that controls a light amount of the irradiation light onto the subject and an electronic shutter of the image sensor based on the luminance level, and the dimming control unit executes first dimming control of narrowing the electronic shutter before reducing the light amount as the luminance level becomes larger.

(11) A medical observation system including: an image sensor that captures a subject image introduced by an endoscope; a light source device that supplies irradiation light onto a subject; and a medical control device that controls operation of the image sensor and the light source device, in which the medical control device includes a captured image acquisition unit that acquires a captured image generated by the image sensor, a luminance calculation unit that calculates a luminance level of the subject image included in the captured image, and a dimming control unit that controls a light amount of the irradiation light onto the subject and an electronic shutter of the image sensor based on the luminance level, and the dimming control unit executes second dimming control of reducing the light amount before narrowing the electronic shutter as the luminance level increases.

With the medical control device and the medical observation system according to the present disclosure, it is possible to effectively suppress fogging caused in the optical member provided at the distal end of the endoscope.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control device comprising:
captured image acquisition circuitry configured to acquire a captured image generated by an image sensor capturing a subject image introduced by an endoscope;
luminance calculation circuitry configured to calculate a luminance level of the subject image included in the captured image;
type determination circuitry configured to determine a type of the endoscope in accordance with where the endoscope is to be inserted; and
dimming control circuitry configured to
control a light amount of irradiation light onto a subject and an electronic shutter of the image sensor based on the luminance level,
in response to insertion of the endoscope to be internal to a subject, execute first dimming control in a case where the type of the endoscope is a first type, the first dimming control including narrowing the electronic shutter before reducing the light amount as the luminance level increases, and
in response to insertion of the endoscope to be external to the subject, execute second dimming control different from the first dimming control in a case where the type of the endoscope is a second type different from the first type, the second dimming control includes reducing the light amount before the electronic shutter is narrowed as the luminance level increases.

2. The medical control device according to claim 1, wherein
the first type is an endoscope for an abdominal cavity, and
the second type is an endoscope for otology.

3. The medical control device according to claim 1, wherein the type determination circuitry is configured to determine the type of the endoscope based on at least one of a region of the subject image included in the captured image and a mask region other than the subject image included in the captured image.

4. The medical control device according to claim 1, wherein a maximum value of the light amount in the first dimming control is larger than a maximum value of the light amount in the second dimming control.

5. The medical control device according to claim 1, wherein a minimum value of the light amount in the first dimming control is larger than a minimum value of the light amount in the second dimming control.

6. The medical control device according to claim 1, wherein the dimming control circuitry is configured to decrease a gain of at least one of an analog gain for an analog signal corresponding to the captured image and a digital gain for a digital signal corresponding to the captured image before narrowing the electronic shutter, as the luminance level increases in the first dimming control and in the second dimming control.

7. The medical control device according to claim 6, wherein the dimming control circuitry is further configured to decrease the analog gain to a minimum analog gain level and to decrease the digital gain to a minimum digital gain level before narrowing the electronic shutter, as the luminance level increases, in the first dimming control and in the second dimming control.

8. The medical control device according to claim 6, wherein the dimming control circuitry is further configured to decrease the analog gain to a minimum analog gain level before reducing the light amount, as the luminance level increases, in the first dimming control and in the second dimming control.

9. The medical control device according to claim 1, wherein a maximum value of the light amount in the first dimming control is sufficient to suppress fogging of the endoscope and a maximum value of the light amount in the second dimming control is less than the maximum value of the light amount in the first dimming control.

10. A medical observation system comprising:
an image sensor configured to capture a subject image introduced by an endoscope;
a light source configured to emit irradiation light onto a subject; and
a medical control device configured to control operation of the image sensor and the light source, the medical control device including captured image acquisition circuitry configured to acquire a captured image generated by the image sensor, luminance calculation circuitry configured to calculate a luminance level of the subject image included in the captured image, type determination circuitry configured to determine a type of the endoscope in accordance with where the endoscope is to be inserted; and dimming control circuitry configured to control a light amount of irradiation light onto a subject and an electronic shutter of the image sensor based on the luminance level, in response to insertion of the endoscope to be internal to a subject, execute first dimming control in a case where the type of the endoscope is a first type, the first dimming control including narrowing the electronic shutter before reducing the light amount as the luminance level increases, and in response to insertion of the endoscope to be external to the subject, execute second dimming control different from the first dimming control in a case where the type of the endoscope is a second type different from the first type, the second dimming control includes reducing the light amount before the electronic shutter is narrowed as the luminance level increases.

11. The medical observation system according to claim 10, wherein the first type is an endoscope for an abdominal cavity, and the second type is an endoscope for otology.

12. The medical observation system according to claim 10, wherein the type determination circuitry is configured to determine the type of the endoscope based on type information that is stored in a memory provided in the endoscope and indicates the type of the endoscope.

13. The medical observation system according to claim 10, wherein a maximum value of the light amount in the first dimming control is larger than a maximum value of the light amount in the second dimming control.

14. The medical observation system according to claim 10, wherein a minimum value of the light amount in the first dimming control is larger than a minimum value of the light amount in the second dimming control.

15. The medical observation system according to claim 10, wherein the dimming control circuitry is configured to decrease a gain of at least one of an analog gain for an analog signal corresponding to the captured image and a digital gain for a digital signal corresponding to the captured image before narrowing the electronic shutter, as the luminance level increases, in the first dimming control and in the second dimming control.

16. The medical observation system according to claim 15, wherein the dimming control circuitry is configured to decrease the analog gain to a minimum analog gain level and to decrease the digital gain to a minimum digital gain level before narrowing the electronic shutter, as the luminance level increases, in the first dimming control and in the second dimming control.

17. The medical observation system according to claim 15, wherein the dimming control circuitry is further configured to decrease the analog gain to a minimum analog gain level before reducing the light amount, as the luminance level increases, in the first dimming control and in the second dimming control.

18. A method of controlling dimming in a medical control device, the method comprising:

calculating a luminance level of a subject image introduced by an endoscope and captured by an image sensor;

determining a type of the endoscope in accordance with where the endoscope is to be inserted; and controlling a light amount of irradiation light onto a subject and an electronic shutter of the image sensor based on the luminance level, in response to insertion of the endoscope to be internal to a subject, executing first dimming control in a case where the type of the endoscope is a first type, the first dimming control including narrowing the electronic shutter before reducing the light amount as the luminance level increases, and in response to insertion of the endoscope to be external to the subject, executing second dimming control different from the first dimming control in a case where the type of the endoscope is a second type different from the first type, the second dimming control includes reducing the light amount before the electronic shutter is narrowed as the luminance level increases.

19. The method according to claim 18, further comprising, as the luminance level increases, before narrowing the electronic shutter in the first dimming control and in the second dimming control:

decreasing an analog gain for an analog signal corresponding to the subject image to a minimum analog gain level; and decreasing a digital gain for a digital signal corresponding to the subject image to a minimum digital gain level.

20. The method according to claim 18, wherein a maximum value of the light amount in the first dimming control is sufficient to suppress fogging of the endoscope and a maximum value of the light amount in the second dimming control is less than the maximum value of the light amount in the first dimming control.

* * * * *